United States Patent [19]

Sperner

[11] 4,326,889

[45] Apr. 27, 1982

[54] DENTAL COMPOSITION FROM GOLD PARTICLES, TERPINEOL AND ETHYL CELLULOSE

[75] Inventor: Franz Sperner, Hanau am Main, Fed. Rep. of Germany

[73] Assignee: W. C. Heraeus GmbH, Hanau, Fed. Rep. of Germany

[21] Appl. No.: 82,673

[22] Filed: Oct. 9, 1979

[30] Foreign Application Priority Data

Nov. 30, 1978 [DE] Fed. Rep. of Germany ....... 2851729

[51] Int. Cl.³ ........................... C08K 3/08; C08K 5/05
[52] U.S. Cl. ....................................... 106/35; 433/200
[58] Field of Search .................. 106/35, 1.13; 433/200

[56] References Cited

U.S. PATENT DOCUMENTS

| | | | |
|---|---|---|---|
| 324,650 | 8/1885 | Buatt | 106/35 |
| 1,040,838 | 10/1912 | Alexander | 106/35 |
| 2,980,998 | 4/1961 | Coleman et al. | 106/35 |
| 4,162,163 | 7/1979 | Subelka | 106/35 |

Primary Examiner—Harold D. Anderson
Attorney, Agent, or Firm—Frishauf, Holtz, Goodman & Woodward

[57] ABSTRACT

Essentially spherical gold particles are mixed with an evaporatable or combustible paste-forming material, for example terpineol and ethylcellulose, the gold being, by weight, 75% to 95%, spherical, and having a diameter of between 0.8 to 1.2 μm, with a maximum particle diameter of 2 μm. The gold is mixed with the additives to form a paste, just before being applied at a thickness of from between 5 to 30 μm on a dental prosthesis, preferably about 10 to 20 μm, and then fired at a temperature of between about 950° C. to 1070° C. for a period of between 2–5 minutes, preferably about 960° to 1000° C. of from between 2–3 minutes, providing an excellent base for application of a porcelain layer thereto.

2 Claims, No Drawings

DENTAL COMPOSITION FROM GOLD PARTICLES, TERPINEOL AND ETHYL CELLULOSE

The present invention relates to dentistry, and more particularly to a dental blending gold, a method of applying blending gold to a dental prosthesis for subsequent application thereto of a dental porcelain or ceramic, and to the dental prosthesis article thus made.

BACKGROUND AND PRIOR ART

When making dental prosthesis or parts thereof, it is customary to utilize as base material cast or sintered alloys of various types, such as precious metal alloys having a gold or palladium base, or other alloys, particularly having a nickel or cobalt base. These metallic base materials are then coated, at least in part, with a dental porcelain or similar ceramic so that the appearance of the prosthesis will simulate natural teeth, or match other teeth. The base materials on which the dental porcelain is applied must meet various specification.

The necessary strength required for dental prosthesis is obtained by adding to alloys based on gold various metals of the platinum group of the elements of the periodic system, and non-precious metals such as indium, tin, and iron, in selected proportions. The non-precious metals are believed to favor adhesion of dental porcelain by formation of oxides.

It is customary, when making a dental prosthesis, to first make the base prosthesis of the desired metal by a casting or sintering process. The metallic prosthesis is then exposed to firing in an oxidizing atmosphere, at normal or reduced pressure, and at a temperature of between 950° to 980° C. The surface of the prosthesis then will have a layer of a non-precious metal oxide formed thereon, the layer having a thickness which is difficult to control. If the time of firing and oxidation is increased, the thickness of the oxide layer will likewise increase, and subsequent dental porcelain applied to the oxidized layer will not adhere well. The non-precious metal oxides have a dark coloration, and if the porcelain layer is thin, the teeth will appear grey. It has been proposed to apply a thin blending layer of blending gold to obtain a gold-colored surface of the cast or sintered prosthesis when made with a gold-based alloy, and simultaneously to increase the adhesive force of the dental porcelain thereto. The blending gold is applied on the cast or sintered metallic dental prosthesis before application of the dental porcelain thereto.

Commerically available blending golds are highly temperature sensitive. If the furnace temperatures are too low, that is, are below about 1060° C., the metallic dental prosthesis will have only a matte or dull yellow surface which is discontinuous. An increase in firing temperature leads to formation of drops of the gold layer, that is, the gold runs together to form drops leaving surface areas of the dental prosthesis uncovered in the spaces between the drops and, due to the formation of non-precious metal oxides, leaving a dark coloration.

THE INVENTION

It is an object to provide a blending gold composition which can be applied to metallic dental prosthesis, or parts thereof, in a wide temperature range and which will result in uniform coating or covering of gold, without the formation of drops; to provide a method for application of the blending gold, and, overall, to provide a dental prosthesis on which the ceramic or porcelain coating can be applied which will not have a greyish tint due to shine-through of an underlying non-precious metal oxide.

Briefly, in accordance with a feature of the invention, the blending gold has a gold proportion of about 75 to 95%, in which the gold itself, or at least 95% thereof, is in spherical form, with an average particle size of from between 0.8 to 1.2 $\mu$m, and a maximum particle size of 2 $\mu$m. The blending gold is mixed with an oil which essentially consists of terpineol with ethylcellulose added thereto, to make a paste. The ethylcellulose may comprise only about 7.3% of the paste-forming material which is the remainder of the blending gold.

All percentages herein are by weight.

The blending gold can readily be applied in a thin coating of from between 5 to 30 $\mu$m thickness with a brush on a metallic cast or sintered dental prosthesis. In accordance with a feature of the invention, the metallic dental prosthesis has this blending gold paste applied thereto and is then fired at a temperature of between 950° to 1070° C. for between 2 to 5 minutes. In a particularly preferred form, a layer of from between 10 to 20 $\mu$m thickness of blending gold is applied, and is then fired at from 960° to 1000° C. for 2-3 minutes. Base materials for the dental prosthesis which are particularly suitable for cooperation with the blending gold are, especially, prosthesis having a major component of gold and which, besides one or more metals of the platinum group of the elements of the periodic system, include at least one non-precious metal of the group of indium, tin, gallium, germanium, and iron.

A firing temperature of the blending gold of about 960° C. for about 2 minutes has been found to be adequate to provide a gold-colored, shiny layer on a dental prosthesis, which is continuous and dense. It is believed that, during the firing process, non-precious metal components such as indium and tin diffuse outwardly from the material of the dental prosthesis through the blending gold layer without, however, forming visible oxides at the surface of the blending gold layer. Additionally, gold from the blending gold layer will diffuse into the metallic dental prosthesis to securely anchor the materials to each other. A later-applied coating of porcelain, and fired thereon, resulted in excellent junction of the coating made with the blending gold.

The arrangement in accordance with the present invention has the further advantage of the formation of a dense, uniform gold layer which does not run together to form drops and, additionally, fills slight surface discontinuities, such as scaling, scoring, or grinding marks, which may have resulted from grinding of the base prosthesis, and further filling casting pores which may be open to the surface of the dental prosthesis. These pores, openings, or discontinuities are filled and sealed so that one of the dangers which arises upon subsequent application of dental porcelain, namely the formation of bubbles in the porcelain, is essentially avoided.

EXAMPLE 100 g of gold particles of spherical form and having an average particle diameter of 0.9 $\mu$m, are mixed with 10 g of an oil, the major component of which is terpineol, and which includes 7.3% of ethylcellulose. The mixture is applied to a roller mill for homogenizing. Just before application of the mixture on the metallic dental prosthesis, or a part thereof, a drop of terpineol is added in order to obtain a paste which can be easily spread; the drop of terpineol is mixed with the paste, and the paste then applied with a brush in form of a thin layer of the dental prosthesis.

Particularly good results have been obtained when the base material of the dental prosthesis, or its part, to which the blending gold in accordance with the example is applied, has one or the other of the following compositions:

(1)

Au 39 to 83%
Pt 0 to 16%
Pd 0 to 45%
Ag 0 to 20%
In 0.4 to 3.5%
Sn 0 to 5%
Fe 0 to 0.4%
Cu 0 to 0.4%
Ga 0 to 2%
Ge 0 to 0.5%.
All percentages being by weight.

(2)

Pd 55 to 70%
Ag 25 to 35%
Sn 4 to 6%
In 2.5 to 3.5%
Ga 0 to 2%
Cu 0 to 0.4%
Fe 0 to 0.4%
Ge 0 to 0.5%.
All percentages being by weight.

Two typical prosthetic materials according to Example (1) are:

(3)

Au 70 to 80%
Pt 9 to 16%
Pd 7 to 11%
Ag 0.2 to 1.5%
In 0.7 to 1.5%
Sn 0.5 to 1.2%
Fe 0.1 to 0.3%
Cu 0.1 to 0.4%
All percentages being by weight.

(4)

Au 40 to 50%
Pt 0 to 0.5%
Pd 40 to 45%
In 2 to 3.5%
Sn 2 to 4%
Ga 0.8 to 2%
Ge 0.1 to 0.5%
All percentages being by weight.

A typical material according to Example (2) is:

(5)

Pd 55 to 65%
Ag 27 to 32%
Sn 4 to 6%
In 2.5 to 3%
Ga 0.9 to 1.3%
Cu 0.1 to 0.3%
Fe 0.1 to 0.3%
Ge 0.1 to 0.3%
All percentages being by weight.

Terpineol and ethylcellulose are the preferred materials to mix the gold particles to form the blending gold paste for application to the prosthesis. The gold particles may, however, be mixed with other suspension substances, for example decanol, isotridecyl alcohol and diethylenglycolbutyl-ether; instead of ethylcellulose natural or synthetic resins, for example polymethacrylate, may be used. The common characteristics of all these materials is that, when mixed with gold particles having an average particle diameter of between 0.8 to 1.2 $\mu$m, a maximum of 2 $\mu$m, they form a paste which can readily be applied, for example by brushing, on the prosthesis, and then can be fired, leaving the underlying blending gold fused to the prosthesis.

I claim:

1. A dental gold composition comprising:
   (1) 75% to 95% by weight gold wherein at least 95% of said gold comprises essentially spherical particles having an average particle size of from between 0.8 to 1.2 $\mu$m and a maximum particles size of 2 $\mu$m and,
   (2) the remainder of said composition comprising a paste-forming oil consisting essentially of terpineol and ethyl cellulose, the by weight percentages being based on the weight of the composition.

2. Dental blending gold according to claim 1, wherein the paste-forming oil comprises about 7.3% ethylcellulose.